United States Patent [19]

Gericke et al.

[11] 4,026,144

[45] May 31, 1977

[54] APPARATUS FOR THE GENERATION OF POLYCHROMATIC ULTRASONOGRAPHS

[75] Inventors: Otto R. Gericke, Medfield; Robert C. Grubinskas, Holliston; Roy A. McKeraghan, Brockton, all of Mass.

[73] Assignee: The United States of America as represented by the Secretary of the Army, Washington, D.C.

[22] Filed: Dec. 10, 1975

[21] Appl. No.: 639,528

[52] U.S. Cl. ............................. 73/67.6; 340/5 MP
[51] Int. Cl.² .................................. G01N 29/04
[58] Field of Search .......... 73/67.5 R, 67.5 H, 67.6, 73/67.7, 67.8 R, 67.8 S, 67.9; 340/5 MP; 178/DIG. 18; 343/5 CD

[56] References Cited

UNITED STATES PATENTS

| | | | |
|---|---|---|---|
| 3,156,110 | 11/1964 | Clynes | 73/67.8 |
| 3,564,904 | 2/1971 | Brenden et al. | 73/67.5 H |
| 3,572,088 | 3/1971 | Gericke et al. | 73/67.6 |
| 3,587,298 | 6/1971 | Jacobs | 73/67.6 |

Primary Examiner—Herbert Goldstein
Assistant Examiner—John P. Beauchamp
Attorney, Agent, or Firm—Nathan Edelberg; Robert P. Gibson; Lawrence E. Labadini

[57] ABSTRACT

Apparatus for a color coded visualization of ultrasonic field patterns representing differences in acoustical impedance within a solid or liquid body. Colored ultrasonic images are obtained in response to a multifrequency interrogation of a test specimen by a multifrequency energization of an ultrasonic transducer with indications of characteristic color being obtained at the loci of discontinuities or inhomogeneities in the specimen (solid and/or liquid) being examined. Colored images are provided by an electronic superposition of images on a color television monitor subsequent to the images being color encoded in accordance with at least two, but preferably the three primary colors of red, green and blue.

11 Claims, 1 Drawing Figure

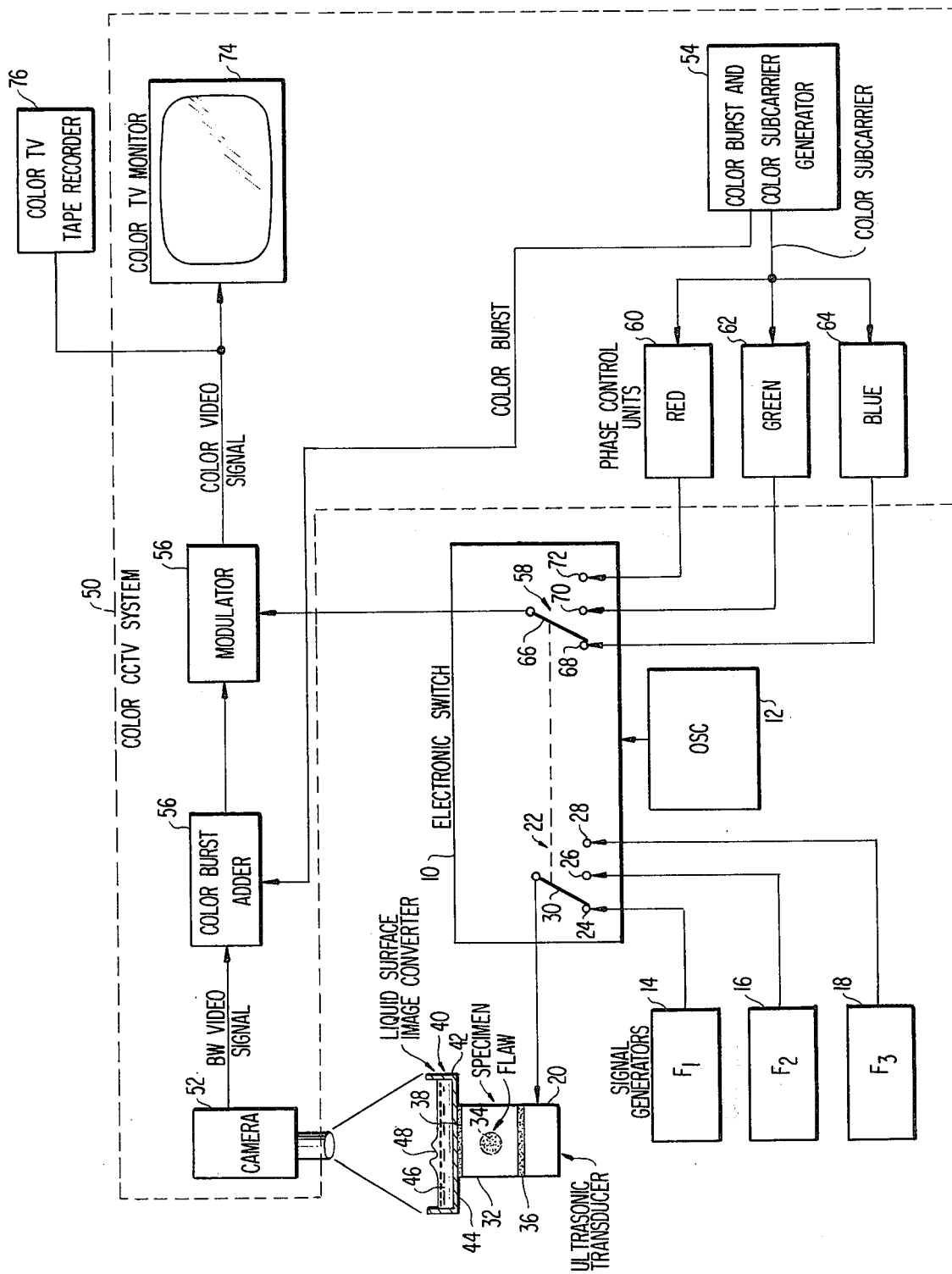

APPARATUS FOR THE GENERATION OF POLYCHROMATIC ULTRASONOGRAPHS

The invention described herein may be manufactured and used by or for the Government for governmental purposes without the payment of any royalties thereon or therefor.

BACKGROUND OF THE INVENTION

This invention relates generally to non-destructive testing apparatus and more particularly to apparatus for providing ultrasonic visualization of discontinuities in optically opaque materials.

As to the prior art, the usual means employed for ultrasonic imaging for determining concealed defects in materials utilizes a tank filled with water or oil in which both the specimen and ultrasonic transmitter are immersed. This necessitates the use of cumbersome test apparatus and the fact that the test specimen and ultrasonic transmitter are immersed in a liquid bath results in accompanying undesirable corrosion effects. This problem was recognized and overcome by apparatus disclosed in U.S. Pat. No. 3,572,088 entitled "Device for Conversion of Ultrasonic Images Into Visible Displays", O. R. Gericke, (the present co-inventor), et al. dated Mar. 23, 1971. There the test specimen is not immersed in a liquid medium. The apparatus disclosed, furthermore, produced monochromatic ultrasonographs which were displayed on a black and white closed circuit television monitor which was subsequently recorded, for example on a video tape recorder.

SUMMARY

The present invention is directed to an improvement in apparatus for ultrasonic visualization of the type disclosed in the aforementioned Gericke, et al. patent and briefly comprises apparatus for sequentially impinging a plurality of ultrasonic frequencies on a specimen, beyond which is located a liquid surface image converter for providing a relief pattern which is a replica of the cross sectional energy distribution of the sequential ultrasonic beams transmitted through the specimen. A TV camera directed at the image converter develops a black and white video signal, representative of the ultrasonic image pattern at each frequency, which is then fed to color television generating apparatus which is synchronously operated in accordance with the application of the plurality of ultrasonic frequencies to provide a respective different color image e.g. red, green and blue, which by rapid superposition on a color television receiver provides an enhancement of the interpretation of the ultrasonic image due to the polychromatic character of the resulting ultrasonograph.

DESCRIPTION OF THE DRAWING

The FIGURE is an electrical block diagram illustrative of the preferred embodiment of the subject invention.

DESCRIPTION OF THE PREFERRED EMBODIMENT

The subject invention utilizes the physical principle that a beam of ultrasonic energy incident upon a free liquid surface will distort the surface to form a relief pattern which is a replica of the cross-sectional energy distribution of the ultrasonic beam. This effect is known as liquid surface levitation.

Referring now to the subject invention and the block diagram shown in the FIGURE, the heart of the system comprises electronic switch means 10 of any desired type adapted to operate as a double-pole three-position switch driven, for example, by an oscillator 12 of predetermined frequency, such as 60Hz, for sequentially switching three frequencies $f_1$, $f_2$ and $f_3$ provided by signal generators 14, 16 and 18 to an ultrasonic transducer 20 and generating red, green and blue TV images respectively for the three frequencies applied to the transducer.

More particularly, the signal generators 14, 16 and 18 are coupled to one section 22 of the electronic switch means 10 which are shown for purposes of explanation as a mechanical switch device having three fixed contacts 24, 26 and 28 and a movable switch contact 30. The three frequencies $f_1$, $f_2$ and $f_3$ are sequentially applied to the ultrasonic transducer 20 at a repetition rate determined by the frequency of the oscillator 12. The transducer 20 is coupled to a test specimen 32 containing a flaw 34 by means of a layer of glycerine 36 positioned between and in contact with the ultrasonic transducer in the manner shown in the above-referenced Gericke, et al. U.S. Pat. No. 3,572,088. On the opposite side of the specimen 34 is located a second glycerine layer 38 which acts as a coupling means to a liquid surface image converter 40 which is comprised of, for example, a metallic cylindrical vessel 42 having a thin, flexible plastic membrane 44 forming a bottom wall adjacent the test specimen 32 and containing a relatively thin layer of image conversion liquid 46.

Internal defects such as cavities or inclusions of foreign matter in the test specimen as indicated by the flaw 34, tends to scatter or absorb ultrasonic intensity and thus modulate the beams being propagated through the specimen, thus producing characteristic relief patterns on the surface of the conversion liquid 46.

In operation, the ultrasonic transducer 20 propagates three separate ultrasonic beams in time sequence through the test specimen 32 to produce respective relief characteristics on the surface of the conversion liquid 46 as generally indicated by reference numeral 48.

A closed circuit color TV system 50 is utilized in combination with the apparatus thus described for generating separate color displays for each of the relief patterns occurring on the surface of the conversion liquid 46 for the three frequencies $f_1$, $f_2$ and $f_3$. The color system 50 disclosed operates upon the well known field sequential principle of color television and includes a TV camera 52 positioned so that its field of view encompasses the surface of the conversion liquid 46. The output of the camera 52 comprises a black and white video signal representing the ultrasonic image pattern observed as the three frequencies $f_1$, $f_2$ and $f_3$ are sequentially applied to the transducer 20 at a 60Hz repetition rate.

As is well known in the art of conventional color television (NTSC system), chromaticity information is contained in a phase modulated subcarrier signal which is combined with a luminance or black and white signal, with a color burst of the subcarrier frequency being transmitted during the synchronizing interval to provide a reference phase of the subcarrier for use in the demodulation of the chrominance-modulated signal in the receiver. Accordingly, a subcarrier generator 54 couples a color burst signal to an adder circuit 56 for inserting a burst of the subcarrier to each horizontal line of the black and white video signal from the camera 52. The three separate ultrasonic images generated by the frequencies $f_1$, $f_2$ and $f_3$ are next caused to produce respective red, green and blue color video signals in the following manner. The subcarrier signal from the subcarrier generator 54 is applied to a phase modulator 56 through a second switch section 58 of the switch means 10 whereupon proper phase relationships well known to those skilled in the art are applied to the field portions of the video signals for $f_1$, $f_2$ and $f_3$ by means of the phase control units 60, 62 and 64 whereupon red, green and blue color video signals are produced sequentially as contact 66 goes through its three positions of the fixed contacts 68, 70 and 72 at a 60Hz rate.

Thus the TV camera 52 in conjunction with the ultrasonic image converter 40 develops a black and white video signal representing the ultrasonic image pattern, whereupon a color burst signal is added to each horizontal line of the black and white video signal. Each field portion of the video signal is then modulated with the color subcarrier signal of a predetermined phase which in accordance to the position of the second segment 58 of the electronic switch means 10, produces a red, green and blue video signal which by means of a color TV monitor 74 coupled thereto, provides a rapid superposition of the three colored images. Additionally, color TV tape recording apparatus 76 can also be coupled to the color video output of the modulator 56.

Thus the displayed image is altered in synchronism with the changing of the ultrasonic frequency and as a result the composite image blends into the color white if the ultrasonic information is not affected by a change in ultrasonic frequency. Frequency dependent differences, on the other hand, produce characteristic hues which indicate how a specific area of the specimen interacts with the wavelength of the interrogating ultrasonic signal. Accordingly, the present invention provides an assessment of the spectral response of a test specimen to ultrasonic signals of different frequencies which is a considerable advantage over prior art ultrasonic imaging methods and apparatus operating at only one frequency. The color encoded multifrequency interrogation of the specimen results in a coloration of the defect outline that is characteristic of its geometry and thereby provides a considerable enhancement of the interpretation of the image.

It is to be pointed out that the present invention has been described in terms of a specific embodiment for purposes of illustration, and it is not meant to be interpreted in a limiting sense, since when desirable, other modifications may be resorted to without departing from the spirit and scope of the invention. For example, the ultrasonic transducer 20 is shown coupled to the test specimen 32 in an ultrasonic through-transmission configuration using compressional waves. When desirable, reflection techniques, shear wave and surface wave modes of operation are also possible. Additionally, by appropriately increasing the speed of the electronic switch 10 by means of varying the frequency of the oscillator 12, the system can be made to operate as dot sequential or line sequential systems instead of a field sequential system. Intermediate speeds are also feasible. A dot sequential operation would be advisable if the system is to be used with an ultrasonic scanning method in which the test specimen is interrogated in a point-by-point fashion. With exception of the switching rate of the electronic switch means 10, no modifications of the circuitry are required.

Having thus disclosed what is at present considered to be the preferred embodiment of the subject invention,

We claim:

1. In ultrasonic test apparatus wherein images are derived from the ultrasonic interrogation of a test specimen, the combination of:
    an ultrasonic transducer;
    a plurality of signal generators each providing an output signal of a selected different frequency;
    means sequentially cooling said plurality of signal generators to said ultrasonic transducer at a predetermined repetition rate whereby each of said output signals causes said transducer to produce an ultrasonic wave of the respective output frequency of said plurality of signal generators;
    means coupling said plural frequency ultrasonic waves to said test specimen;
    ultrasonic image converter means coupled to said test specimen and being responsive to said ultrasonic waves of different frequencies following the influence of said test specimen thereon to provide a separate ultrasonic image for each frequency of said plurality of signal generators; and
    a polychromatic imaging system operating in synchronism with said sequential coupling means coupled to said image converter and being responsive to the ultrasonic images provided thereby to generate a visual image of a separate color for each frequency of said plurality of signal generators.

2. The apparatus as defined by claim 1 wherein said ultrasonic image converter means includes a conversion liquid providing relief patterns of said specimen formed on the surface in response to the ultrasonic beam being directed through said test specimen from said transducer.

3. The apparatus as defined by claim 2 wherein said polychromatic imaging system superimposes each visual image to provide a polychromatic composite image.

4. The apparatus as defined by claim 3 wherein said polychromatic imaging system comprises a color television system including a television camera optically coupled to said ultrasonic image converter means.

5. The apparatus as defined by claim 4 wherein said television camera provides a black and white video signal output therefrom.

6. The apparatus as defined by claim 5 wherein said color television system comprises a field sequential system including means for adding a color burst signal to each horizontal line of the black and white video output signal from said camera and for selectively and sequentially phase modulating the field portion of the black and white video signal with a color subcarrier signal for each of said selected different frequencies.

7. The apparatus as defined by claim 4 wherein said plurality of signal generators comprises at least three signal generators operating at the respective frequencies $f_1$, $f_2$ and $f_3$ and wherein said color television system is adapted to provide respective visual images for the frequencies $f_1$, $f_2$ and $f_3$ corresponding to the three primary colors of red, green and blue.

8. The apparatus as defined by claim 7 wherein said means for sequentially coupling said plurality of signal generators to said ultrasonic transducers comprises electronic switch means and additionally including an oscillator operating at said predetermined repetition rate coupled to and operating said electronic switch means.

9. The system as defined by claim 8 wherein said color television system additionally includes a color subcarrier generator providing a color burst signal and a color subcarrier signal, wherein said camera provides a video signal output, and additionally including circuit means for adding a color burst signal to said video signal output, phase modulator means coupled to said video signal, and means for sequentially coupling said color subcarrier signal in predetermined phase relationships to said phase modulator means thereby providing three primary color video output signals for the frequencies $f_1$, $f_2$ and $f_3$ and additionally including means responsive to said color video signals coupled to said phase modulator means for displaying superposed visual images.

10. The apparatus as defined by claim 9 wherein said means responsive to said color video signals comprises a color television receiver.

11. The apparatus as defined by claim 10 and additionally including color television recording means coupled to said phase modulator means.

* * * * *